United States Patent [19]

Etter

[11] Patent Number: 5,050,437
[45] Date of Patent: Sep. 24, 1991

[54] APPARATUS FOR DETERMINING STRENGTH PROPERTIES OF LONG TEXTILE TEST MATERIAL

[75] Inventor: Heinz Etter, Winterthur, Switzerland

[73] Assignee: Zellweger Uster AG, Uster, Switzerland

[21] Appl. No.: 540,338

[22] Filed: Jun. 19, 1990

[30] Foreign Application Priority Data

Jun. 20, 1989 [CH] Switzerland ............... 2292/89

[51] Int. Cl.⁵ .................................................. G01N 3/08
[52] U.S. Cl. ........................................ 73/830; 73/831
[58] Field of Search ............... 73/160, 826, 828–831, 73/833, 834, 856, 860, 830, 831

[56] References Cited

U.S. PATENT DOCUMENTS 4,601,208 7/1986 McKay et al. ........................ 73/829
4,825,702 5/1989 Cizek ..................................... 73/828

FOREIGN PATENT DOCUMENTS 737522 7/1943 Fed. Rep. of Germany ........ 73/160

Primary Examiner—Robert Raevis
Attorney, Agent, or Firm—Burns, Doane, Swecker & Mathis

[57] ABSTRACT

Yarn tensile textile apparatus contains drawing-off means (11) for continuously drawing-off the test material (G) from a supply, two roller pairs (W, W') at a distance from one another for elongating the test material (G), and a store (12) arranged between the drawing-off means (11) and the first roller pair (W). Each roller pair (W, W') contains a transport roller and a pressing roller (4, 5; 4', 5') arranged so that a periodically opening and closing clamping gap for the test material (G) is formed between the rollers of each roller pair. Each transport roller (4, 4') includes a first circumferential part for bearing against its pressing roller (5, 5') and a second circumferential part at a distance from its pressing roller (5, 5'). The apparatus permits tensile testing according to the principle of constant rate of deformation, and the apparatus is insensitive to soiling and can be used for testing a variety of test materials.

23 Claims, 3 Drawing Sheets

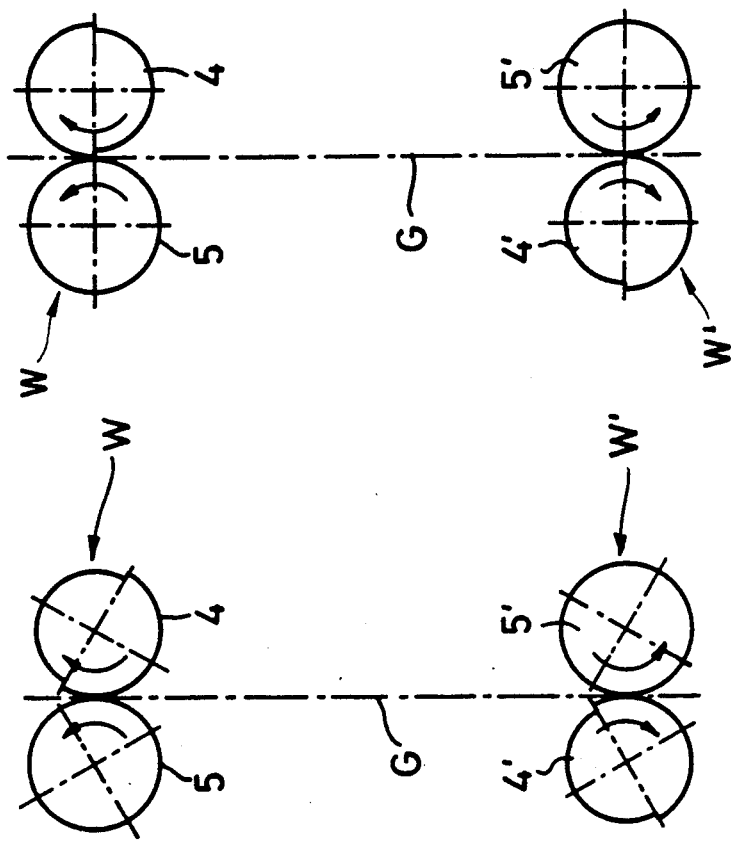

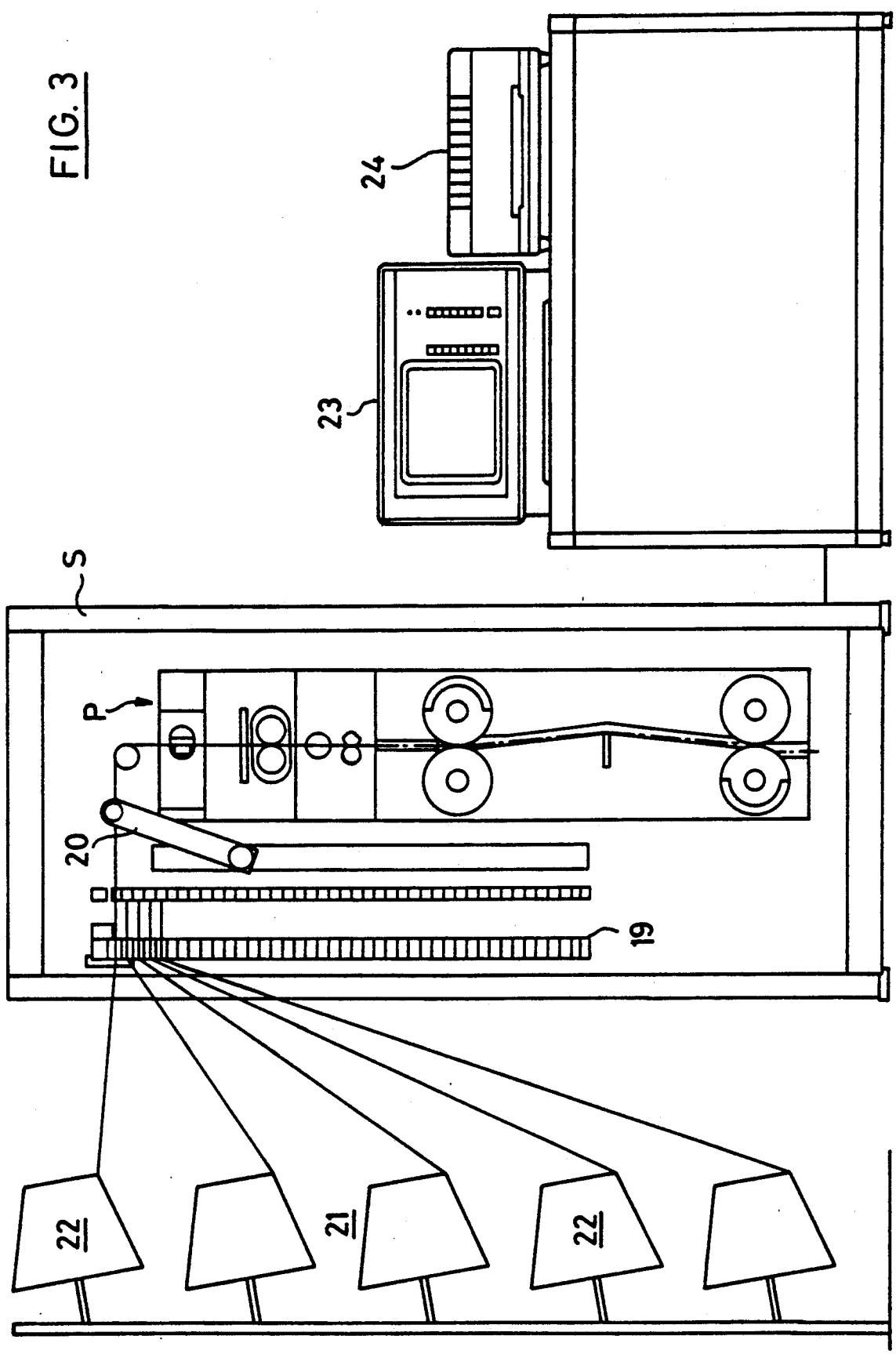

APPARATUS FOR DETERMINING STRENGTH PROPERTIES OF LONG TEXTILE TEST MATERIAL

FIELD OF THE INVENTION

The present invention relates to an apparatus for determining strength properties of long textile test material such as yarn. It is concerned particularly with a system of the type comprising drawing-off means for continuously drawing-off the test material from a supply, two driveable clamping members at a distance from one another and each having a rotatable roller for elongating the fed test material by means of rotation of the rollers, and a store arranged between the drawing-off means and the first clamping member in the running direction of the test material.

BACKGROUND

An apparatus of this general type is disclosed in EP-A-241,894 and its counterpart U.S. Pat. No. 4,825,702. In this apparatus each clamping member has a band (in practice, a steel band) which is in contact around the roller through 180°. The test material is inserted into the gap between band and roller and clamped in place between these by the rotation of the roller and the band, the clamping length reaching at most half the periphery of roller.

With this apparatus continuous testing of strength properties is made possible. The test material is continuously drawn-off from its supply and fed intermittently to the driven clamping members during the testing operation. A higher test speed is reached than in such tensile-testing installations as the apparatus sold by Zellweger Uster AG under the trademark USTER TENSORAPID.

The testing of strength properties, that is, maximum tensile force (breaking strength) and elongation, was for a long time regulated by a plurality of national and international standards. A new standard DIN 53834, which only permits the so-called CRE-Principle (CRE=Constant Rate of Elongation, or, in other words, constant rate of deformation), was introduced in 1976. In this respect, reference is made to the publication USTER News Bulletin No 26, November 1978 "USTER Prüfverfahren für das leistungsstarke Textillabor" (USTER Test Methods for the efficient textile laboratory), Page 32 ff.

The apparatus described in EP-A-241,894 and U.S. Pat. No. 4,825,702, has the considerable disadvantage that it does not permit any testing according to the CRE-Principle owing to the fact that the rate of deformation greatly depends on the elongation. In fact the profile of the rate of deformation is sinusoidal. The rate of deformation increases from zero when the test material is clamped in place up to a maximum value at a 90° angle of contact on the rollers and then reaches zero again at 180°. Other disadvantageous properties of this known apparatus also exist. Ever slight soiling between roller and band impairs the measuring accuracy. Moreover, the clamping principle that is used does not permit any large tensile forces. The latter means restriction with regard to the test material.

SUMMARY OF THE INVENTION

According to the present invention, each clamping member is formed by a roller pair having surfaces which alternately bear against and are spaced apart from one another to provide a periodically opening and closing clamping gap for the textile test material.

The CRE-Principle is complied with by the features according to the invention, and the strength properties, such as maximum tensile force and elongation, are thus determined according to the principle of constant rate of deformation. This is because the test material, during clamping by the roller pair, is clamped in place at two locally stationary lines of contact between the two rollers. The risk of soiling is substantially less during this clamping than during clamping between rollers and a band, and there are virtually no restrictions with regard to the test material.

In addition, the roller pair is substantially less susceptible to wear than the combination of roller and steel band, and the entire apparatus also becomes substantially more compact. There are fewer individual parts, and an increase in safety is obtained as a result of the steel band being omitted.

BRIEF DESCRIPTION OF THE DRAWINGS

The invention is described in greater detail below with reference to an exemplary embodiment and the drawings, in which:

FIG. 2a, FIG. 2b, FIG. 3c and FIG. 2d are diagrams to explain the function; and

FIG. 3 shows a representation of a testing installation containing an apparatus according to the invention.

DETAILED DESCRIPTION OF PREFERRED EMBODIMENTS

Figure 1:
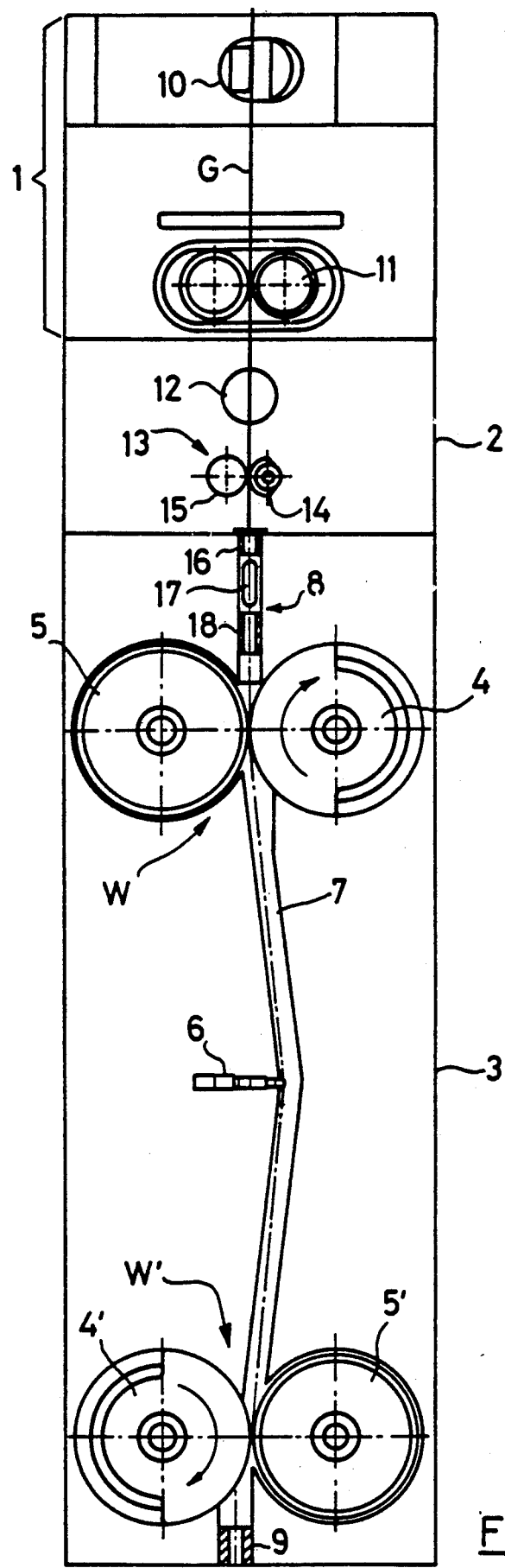
FIG. 1 shows a schematic front view of an apparatus according to the invention.

According to FIG. 1, the elongation and tensile-force testing apparatus essentially consists of a feed part 1 for the yarn G to be tested, a storage part 2 and an actual test part 3. Each of these parts can be designed as module.

The test part contains two roller pairs W and W' at a distance apart, each of which consists of a driveable transport roller 4, 4' and a pressing roller 5, 5'. A slightly bent yarn channel 7 runs between the roller pairs W, W', and a force sensor 6 is arranged at the bending point or apex of the yarn channel 7 to provide a measure of the tension in the yarn being tested. The force sensor 6 is preferably a piezoelectric sensor. The two parts of the yarn channel 7 which are inclined towards one another are of the same length, so that no relative movement develops on the sensor 6. The test part 3 also contains a entry part 8 and an exit part 9 for the yarn G to be tested.

The test part 3 is in the form of a body member (e.g. a plate or block) having a front face covered with a transparent member. The front face, which is visible through the transparent cover member in FIG. 1, has grooves and recesses therein. A groove of generally U-shaped cross-section in the front face of the body member provides the yarn channel 7, and there are recesses for the rollers 4, 5, 4' and 5' as well as the force sensor 6 and its mount. Continuations of the channel above and below the roller pairs W and W' provide seats for the components 8 and 9.

The transparent cover has a generally flat rear face that normally seals against the generally flat front face of the body member and overlies the recesses and grooves to form a passage through which air may flow when a suction source is connected to the exit or outlet part 9. The normally sealing relation of the transparent cover against the front face of the body member prevents the entrance of large amounts of extraneous air during operation of the system, but the cover may be removed from the front face of the body member when access to the yarn channel 7 or the components 4–9 is desired. The cover may be attached to the body member by sliding connectors, hinges, screws or other suitable means.

Essential components of the test part 3 are the two roller pairs W and W', which serve to clamp a fed length of yarn in place and then to load it at a constant rate of deformation until it breaks. For this purpose, each of roller pairs W and W' must be able to perform an opening and closing movement like a conventional thread clamp in order to secure the length of yarn in place and release it. This can be achieved, for example, by a controlled increase and reduction in the distance between the axes of the two rollers 4, 5 and 4', 5' of each roller pair W and W' respectively.

A more preferred approach is indicated in FIG. 1. Here, the distance between the axes of the two rollers is constant, but one of the two rollers, namely the roller 4, 4' designated as transport roller, is of stepped configuration at its periphery and has two peripheral parts of different radii for contacting the yarn being tested. The large radius corresponds to the distance from the axis of the transport roller up to the axis of the pressing roller, reduced by the radius of the latter. The small radius is somewhat smaller. Each of the peripheral parts may extend, for example, over 180° of the circumferential surface of the transport roller 4, 4'.

The transport rollers 4, 4' are driven in a contra-rotating manner in the directions designated by the arrows in FIG. 1. They may be fixed to shafts extending through bearings arranged in the body member of the test part 3 to minimize air leakage. It is preferred that a common drive at the back side of the body member be used to rotate the rolls 4 and 4'. The rollers 4 and 4' are arranged according to the drawing on different sides of the yarn channel 7. Both transport rollers 4 and 4' are driven continuously and run in strict synchronism.

The pressing rollers 5 and 5', which are provided at their circumferential surfaces with a high-modular layer of, for example, rubber, are mounted so as to be freely rotatable and require no special drive. They are mounted to press against the large radius portions of their adjacent transport rollers 4 and 4' with sufficient force to accomplish the desired clamping action, but they are held against contact with the small radius portions of the transport rollers 4 and 4'. The pressing rollers 5 and 5' are driven frictionally by contact with larger radius portions of the transport rollers.

When a yarn G is between a large radius portion of a transport roller 4 or 4' and the associated pressing roller 5 or 5', the yarn G is clamped in place between the two rollers (thread clamp closed). In the other case, there is a gap between the two rollers in the connecting plane between their axes (thread clamp open).

The operations during clamping, elongation and release of a yarn G are shown in FIG. 2 with the aid of four diagrams 2a to 2d. Each diagram schematically shows a piece of yarn G to be tested and the two roller pairs W and W' having the rollers 4, 5 and 4', 5'. The differences between the individual diagrams lie in the respective rotary position of the transport rollers 4, 4'. In diagram 2a, the smaller radius half of each of the transport rollers rotates past the corresponding pressing roller 5, 5' and thus along the yarn G. The clamping gap is therefore open here, and the yarn G is inserted into the open clamping gap.

In diagram 2b, the step between the smaller and the larger radius of the transport rollers 4, 4' just reaches the connecting plane between the roller axes and the phase of mutual contact between the two rollers 4, 5 and 4', 5' starts. At this moment, the yarn G is clamped in place and its elongation starts. In diagram 2c there is still contact between the two rollers 4, 5 and 4', 5'; the elongating action is thus continuing.

In diagram 2d, the step between the larger and the smaller radius of the transport rollers 4, 4' just reaches the connecting plane between the roller axes. This is the moment of greatest elongation of the yarn G, and the clamping of the yarn G is ended immediately afterwards. In practical operation, this greatest elongation of the yarn G is not reached, since the yarn G has already broken beforehand. In other words, the dimensioning and operating parameters of the apparatus are planned in such a way that the particular yarn G always breaks during the elongating action (diagram 2c).

The state according to diagram 2a is then reached again in which the broken yarn part is removed from the apparatus and a new length of yarn is inserted into it. This may be accomplished by a suction applied at the outlet 9. The suction carries away the broken yarn fragment and applies a draft through the yarn channel 7 to thread a new yarn length to be tested from the part 8 down through the thread passage. The suction also holds the new yarn part under a light tension to prevent the formation of undesired loops or the like prior to the moment when the roller pairs W and W' exert the intended clamping actions on the yarn.

The feed part 1 of the apparatus shown in FIG. 1 essentially contains a thread brake 10 and a pair of motor-driveable delivery rollers 11 with which the yarn G is continuously drawn-off from a supply (see FIG. 3). Suitable forms of thread brake 10 and delivery rollers 11 are known to persons skilled in the art and they are not described in greater detail here. Such components are embodied for example in the apparatus sold by Zellweger Uster AG under the trademark USTER TESTER 3.

Although the transport rollers 4, 4' are driven continuously, the method steps consisting of clamping, elongation and release of the yarn nonetheless run discontinuously. Hence, yarn G must not of course be delivered to the roller pair W during the clamping and during the elongation. For this reason, the storage part 2 (which serves to store the continuously delivered yarn G) is provided with a thread store 12 for the discontinuous delivery of the yarn to the roller pair W. In addition, the storage part 2 has a controlled thread clamp 13 which consists of a continuously driven control roller 14 and a freely rotatable mating roller 15. The controlled thread clamp 13 enables controlled emptying of the thread store 12. The control roller 14, like the transport rollers 4, 4', has two peripheral parts of different radii so that the yarn G is either clamped in place or released by the thread clamp 13. The drive of the control roller 14 is coupled to that of the transport rollers 4, 4'; a single drive motor is preferably provided for the delivery rollers 11, the control roller 14 and the transport rollers 4, 4'.

The entry part 8 of the test part 3 serves to convey the yarn G from the thread store 13 into the yarn channel 7. It includes a first suction nozzle 16, an intermediate store 17 and a second suction nozzle 18. If the control roller 14 and the transport roller 4 are driven at the same rotary speed, the linear peripheral speed of roller 4 will be greater than that of roller 14. Hence, yarn fed by roller 4 goes faster than yarn fed by roller 14. The intermediate store 17 in which the corresponding difference in length is stored is therefore provided. The nozzle 18, which preferably operates intermittently in synchronization with the time periods when the roller pairs W and W' are not clamping the yarn, serves to withdraw yarn from the intermediate store 17 and delivers it to the downward threading flow established from the suction applied at the outlet member 9.

Both the thread store 12 and the intermediate store 17 are pneumatic thread stores of the type as known, for example, from air-nozzle weaving machines. Each of these stores is preferably formed by a tubular chamber which extend from the drawing plane to the rear. In the area where the yarn G is directed past its inlet opening, each store has a suitable blowing and/or suction nozzle for conveying the yarn into the storage tube. Particularly suitable for these purposes is a so-called Coanda nozzle of the type described in Swiss Patent Application No. 04539/86-4 corresponding to FR-A-2,606,893.

FIG. 3 shows a complete tensile-testing installation with a testing apparatus according to FIG. 1. According to the representation, the testing apparatus designated by P is fitted into a cabinet-like housing S which in addition contains a thread changer 19 and an insertion arm 20 for inserting the yarn G, spread out on the thread changer 19, into the testing apparatus P. Set up next to the housing S is a bobbin stand 21 having bobbins 22 for the yarn G to be tested. The thread changer 19, insertion arm 20 and bobbin stand 21 may be like these employed in the tensile-testing appliance sold by Zellweger Uster AG under the trademark USTER TENSORAPID.

The measuring signals are analyzed in a signal processor which is preferably fitted into a video display unit 23. The latter, in the same way as a printer 24, serves for the output of results in numerical and graphic form. The video display unit 23 containing the signal processor is known from the USTER TESTER 3 and from the USTER TENSORAPID 3. In this connection, reference is also made to EP-A-249,741.

With testing installations of the type shown in FIG. 3, up to 400 meters of yarn per minute can be tested. The apparatus according to the invention thus permits test speeds which are as high as those of evenness testers, and the possibility of a fully automatic textile laboratory with preferably combined use of evenness tester, tensile-testing installation and number-determining system, perhaps coupled to modules for determining further parameters, presents itself. A multitester of this type would then consist, for example, of a combination of the testing installation shown in FIG. 3 plus the apparatus described in the PCT application WO 89/03531 for determining the evenness and the fineness.

The preferred testing apparatus according to the invention, also has additional advantages. The design permits simple interchange of parts subject to wear, such as, for example, the rollers, and simple rectification of faults such as, for example, in the event of obstructions caused by critical yarn material. Owing to the fact that only a few deflection points are necessary for the insertion of the yarn into the roller pairs and into the measuring section, the flow losses are very low. Consequently, the insertion operation is substantially facilitated and a larger range of yarn materials can be handled with less flow loss.

What is claimed is:

1. Apparatus for determining strength properties of long textile test material comprising drawing-off means for continuously drawing-off the test material from a supply, a store for receiving test material from said drawing-off means, a first drivable clamping assembly for receiving test material from said store, and a second driveable clamping assembly at a distance from said first drivable clamping assembly for receiving test material from said first drivable clamping assembly, each of said clamping assemblies being formed by a roller pair in which the surface of one of the rollers of the pair is alternately in contact with and spaced from the surface of the other roller of the pair as the rollers are rotated, so that each clamping assembly provides a periodically opening and closing clamping gap for the test material, whereby tension for strength property determination is applied to the test material by the clamping assemblies when the clamping gaps are closed.

2. Apparatus according to claim 1, wherein the two rollers forming a roller pair are arranged with a constant distance between their axes, and wherein one roller of the pair is of stepped configuration at its circumferential surface and has two peripheral parts of different radii.

3. Apparatus according to claim 2, wherein the larger radius of said roller of stepped configuration corresponds substantially to the distance between the axes of the two rollers reduced by the radius of the other roller.

4. Apparatus according to claim 3, wherein the rollers of stepped configuration in the two roller pairs are connected to a common drive and are driven in opposite directions.

5. Apparatus according to claim 4, wherein the peripheral parts of different radii each extends over about half the periphery of its roller.

6. Apparatus according to claim 3, wherein a guide channel for the test material is provided between the roller pairs, and a sensor for the measurement of force is provided in said guide channel.

7. Apparatus according to claim 6, wherein the rollers of stepped configuration are disposed on different sides of the guide channel.

8. Apparatus according to claim 6, wherein the guide channel includes two parts which are inclined towards one another, and wherein said sensor is arranged in the transition area between these two parts.

9. Apparatus according to claim 8, wherein said guide channel parts are of the same length.

10. Apparatus according to claim 1, wherein said store is a pneumatic store.

11. Apparatus according to claim 10, including pneumatic means for the transport of the test material from the drawing-off means to the first clamping assembly.

12. Apparatus according to claim 11, including a controlled thread clamp arranged between said store and said first clamping assembly.

13. Apparatus according to claim 12, wherein said controlled thread clamp is formed by a roller pair including a control roller and a mating roller.

14. Apparatus according to claim 13, wherein said control roller has two peripheral parts of different radii, and wherein the test material is clamped in place when bearing against the peripheral part having a larger radius and is released when bearing against the peripheral part having the smaller radius.

15. Apparatus according to claim 14, including a drive for said clamping assemblies, and wherein the control roller has a drive which is connected to said drive for the clamping assemblies.

16. Apparatus according to claim 15, wherein said drive for said control roller also drives said drawing-off means.

17. Apparatus according to claim 14, including an entry part between the control roller and the first clamping assembly, and an exit part after the second clamping assembly.

18. Apparatus according to claim 17, wherein the entry part comprises two nozzles and an intermediate store arranged between them.

19. Apparatus according to claim 18, wherein the nozzles are formed by suction nozzles, and wherein the intermediate store is formed by a pneumatic store.

20. Apparatus according to claim 19, wherein said store has a tubular storage space provided with an inlet opening, said tubular storage space being arranged perpendicularly to the axis of a length of test material directed past said inlet opening.

21. Apparatus according to claim 20, wherein a Coanda nozzle is arranged in the area of the inlet opening of the store.

22. Apparatus according to claim 17, wherein the exit part contains a suction nozzle.

23. Apparatus for determining strength properties of long textile test material comprising drawing-off means for continuously drawing-off the test material from a supply, a store for receiving test material from said drawing-off means, a first drivable clamping assembly for receiving test material from said store, and a second drivable clamping assembly at a distance from said first drivable clamping assembly for receiving test material from said first drivable clamping assembly, at least one of said clamping assemblies being formed by a roller pair in which the surface of one of the rollers of the pair is alternately in contact with and spaced from the surface of the other roller of the pair as the rollers are rotated, so that such clamping assembly provides a periodically opening and closing clamping gap for the test material and so that tension for strength property determination is applied to the test material between the clamping assemblies when said clamping gap is closed.

* * * * *